United States Patent
Simonian

(10) Patent No.: US 11,039,949 B2
(45) Date of Patent: Jun. 22, 2021

(54) ORTHOPEDIC DEVICES

(71) Applicant: Peter T. Simonian, Clovis, CA (US)

(72) Inventor: Peter T. Simonian, Clovis, CA (US)

( * ) Notice: Subject to any disclaimer, the term of this patent is extended or adjusted under 35 U.S.C. 154(b) by 148 days.

(21) Appl. No.: 16/175,489

(22) Filed: Oct. 30, 2018

(65) Prior Publication Data
US 2019/0060102 A1 Feb. 28, 2019

Related U.S. Application Data

(63) Continuation-in-part of application No. 13/791,696, filed on Mar. 8, 2013, now Pat. No. 10,149,779.

(51) Int. Cl.
*A61F 5/00* (2006.01)
*A61F 5/37* (2006.01)
*A61F 5/01* (2006.01)

(52) U.S. Cl.
CPC .......... *A61F 5/3723* (2013.01); *A61F 5/0111* (2013.01); *A61F 5/0127* (2013.01); *A61F 5/0118* (2013.01)

(58) Field of Classification Search
CPC ............ A61G 13/0063; A61G 13/0081; A61G 13/12; A61G 13/125; A61G 13/1235; A61G 13/1245; A61G 13/1265; A61G 13/1275; A61G 7/022; A61G 7/075; A61G 7/0755; A61F 5/37; A61F 5/0111; A61F 5/0113; A61F 5/0127; A61F 5/0118; A61F 5/12; A61B 46/27; A61B 46/13; A47C 20/021
USPC ........................................................ D6/601
See application file for complete search history.

(56) References Cited

U.S. PATENT DOCUMENTS

| | | | |
|---|---|---|---|
| 3,901,228 A * | 8/1975 | Brown ............... | A61G 13/0063 5/651 |
| 3,903,878 A | 9/1975 | Spann | |
| 3,939,829 A | 2/1976 | Spann | |
| 3,946,451 A * | 3/1976 | Spann ................ | A61G 7/0755 5/650 |
| 4,971,041 A | 11/1990 | Milliken et al. | |
| 4,982,745 A * | 1/1991 | Shields .................... | A61F 5/01 128/877 |
| 5,085,214 A * | 2/1992 | Barrett ..................... | A61F 5/01 128/882 |
| 5,765,564 A * | 6/1998 | Ewing .................. | A61G 7/0755 128/845 |
| 6,186,967 B1 * | 2/2001 | Messina ................... | A61F 5/01 128/882 |
| 7,188,382 B1 * | 3/2007 | Taylor .................. | A61G 7/0755 128/882 |
| 7,753,864 B2 * | 7/2010 | Beckwith ............. | A61F 5/0113 602/23 |
| 8,314,283 B2 | 11/2012 | Kingsford et al. | |

(Continued)

*Primary Examiner* — Kim M Lewis
(74) *Attorney, Agent, or Firm* — Carr & Ferrell LLP

(57) ABSTRACT

The present application is directed to methods and devices for reducing shoulder impingement for a person in a lying position. The device may comprise a generally tubular cuff having an inner radius defining an open passage through the cuff and extending from a proximal end to a distal end, an outer radius defining a sidewall thickness between the inner radius and the outer radius, and a length from the proximal end to the distal end. The outer diameter may be selected to provide a sidewall thickness that restricts movement of the arm such that shoulder flexion, extension, adduction, abduction, lateral rotation, and medial rotation are each limited.

19 Claims, 14 Drawing Sheets

(56) References Cited

U.S. PATENT DOCUMENTS

| | | |
|---|---|---|
| 8,394,042 B1 | 3/2013 | Mirza |
| 9,392,874 B2 * | 7/2016 | Shaffer ................ A61G 7/0755 |
| 10,149,779 B2 | 12/2018 | Simonian |
| 2006/0293623 A1 | 12/2006 | Carroll |
| 2011/0005525 A1 | 1/2011 | Barnes et al. |
| 2011/0125242 A1 | 5/2011 | Zahler |
| 2013/0053740 A1 | 2/2013 | Mustafa |
| 2013/0289462 A1 | 10/2013 | Doumas |
| 2014/0251341 A1 | 9/2014 | Simonian |

* cited by examiner

SHOULDER FLEXION (A)
EXTENSION (B)

SHOULDER ADDUCTION (C)
ABDUCTION (D)

SHOULDER ROTATION, LATERAL (E)
MEDIAL (F)

ORTHOPEDIC DEVICES

CROSS REFERENCE TO RELATED APPLICATIONS

This application is a continuation in part and claims the priority benefit of U.S. Non-Provisional patent application Ser. No. 13/791,696 as filed on Mar. 8, 2013 and titled "Arm Cuff for Reducing Shoulder Impingement," which is hereby incorporated by reference in its entirety.

FIELD OF THE INVENTION

The present application is directed generally to methods and devices for limiting arm and foot movement.

BACKGROUND

The shoulder joint is one of the largest joints in the human body and has the greatest range of motion of any joint. The shoulder joint is the area where the head of the humerus bone joins the scapula. While the shoulder joint is considered a ball and socket joint, the socket is relatively shallow. The shallow socket contributes to the joint's range of motion. Other bones that play a crucial role in the functionality of the shoulder include the acromion and coracoids process that project from the scapula and the clavicle that is connected to the acromion by the acromioclavicular ligament.

A variety of soft tissues hold the shoulder joint in place and allow the wide range of motion. These tissues include the rotator cuff which comprises several muscles and tendons surrounding the shoulder joint, bursae which are sacs of fluid that provide protection and lubrication within the rotator cuff, and the glenoid labrum which is a fibrocartilaginous rim around the socket in the scapula. Additionally, many other ligaments, tendons, and muscles assist in the function of the shoulder joint.

Because of the loose fit between the humerus and the scapula, the wide range of motion of the joint, and the general abuse the joint receives, shoulder injuries are common. Strains and tears of ligaments and tendons, and tears of the tissue comprising the rotator cuff are frequent occurrences for people with an active lifestyle or job, as well as the elderly. Injuries may also occur due to a single event such as lifting a heavy object or an accident.

Each of these injuries typically result in a significant amount of pain, particularly when moving the arm. The most intense pain may occur when the arm is moved towards the extremes of motion and soft tissue is impinged between the head of the humerus and the acromion.

SUMMARY

The present application is directed to methods and devices for reducing shoulder impingement for a person in a lying position. The device may comprise a generally tubular cuff having an inner radius defining an open passage through the cuff and extending from a proximal end to a distal end, an outer radius defining a sidewall thickness between the inner radius and the outer radius, and a length from the proximal end to the distal end. The outer diameter may be selected to provide a sidewall thickness that restricts movement of the arm such that shoulder flexion, extension, adduction, abduction, lateral rotation, and medial rotation are each limited.

DETAILED DESCRIPTION

The present application is directed to methods and devices for reducing shoulder impingement for a person in a lying position. The device may comprise a generally tubular cuff having an inner radius defining an open passage through the cuff and extending from a proximal end to a distal end. The open passage may be adapted to releasably engage a forearm of the person therein. The cuff may also have an outer radius defining a sidewall thickness between the inner radius and the outer radius, and a length from the proximal end to the distal end. The outer diameter may be selected to provide a sidewall thickness that, when the cuff is engaged on the forearm of the person, restricts movement of the arm such that shoulder flexion, extension, adduction, abduction, lateral rotation, and medial rotation are each limited.

Figure 1:
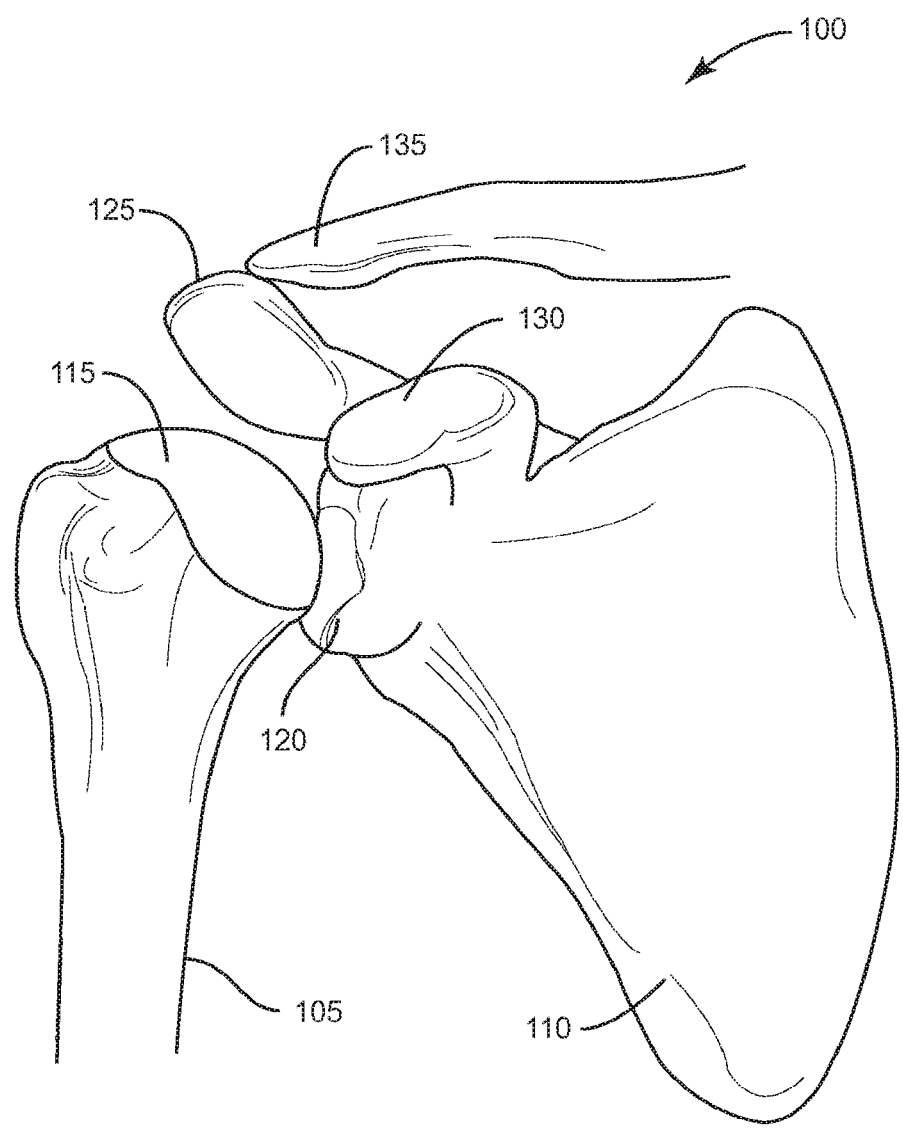
FIG. 1 is an anterior view of the skeletal anatomy of the shoulder.
Figure 2:
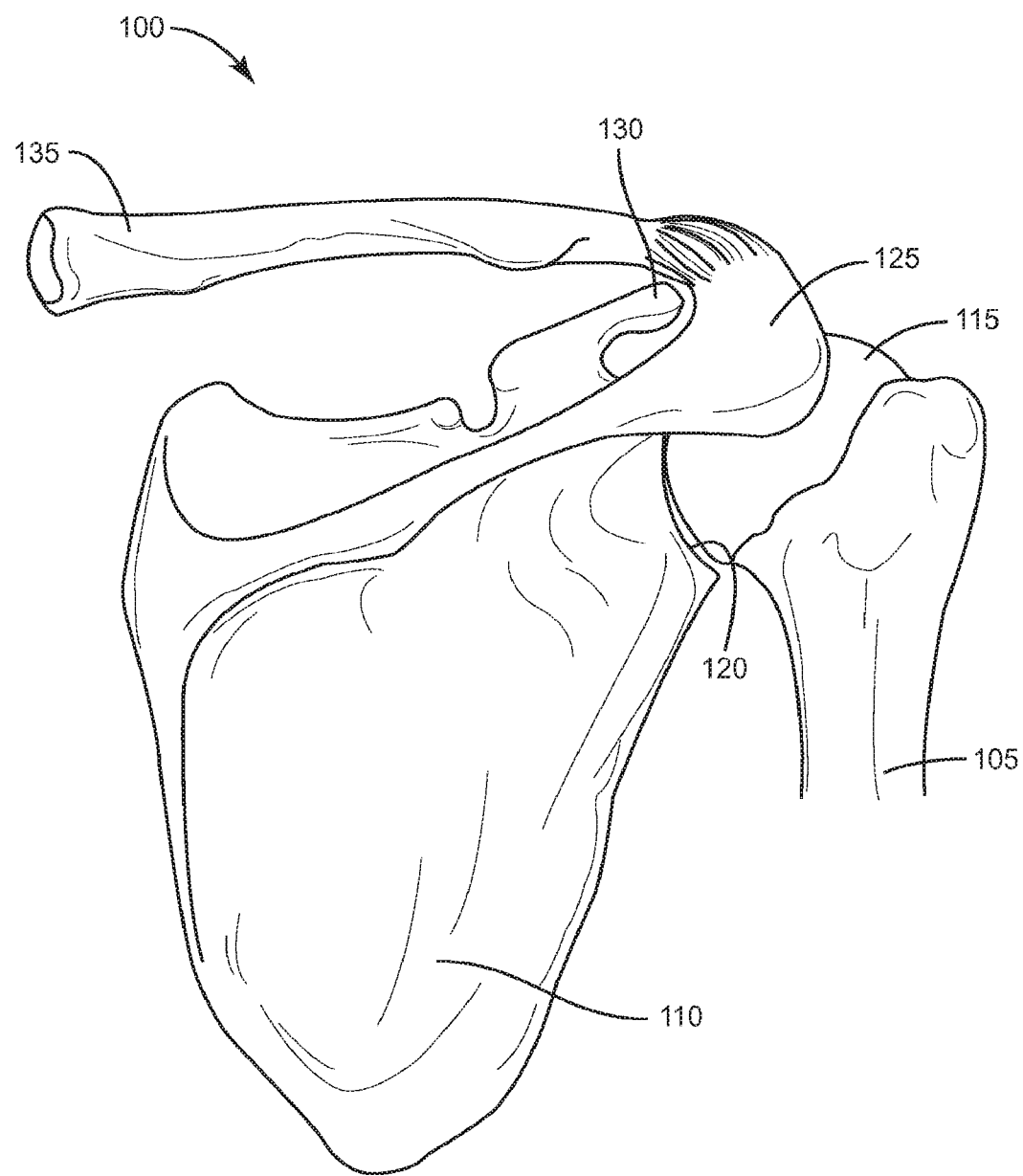
FIG. 2 is a posterior view of the skeletal anatomy of the shoulder.

FIGS. 1 and 2 illustrate anterior and posterior views, respectively, of the skeletal anatomy of the shoulder 100 (also referenced as shoulder joint 100). The shoulder joint is comprised of the humerus 105 (the bone of the upper arm) and the scapula 110 (commonly referred to as the shoulder blade). A terminal portion of the humerus, or the head of the humerus 115, mates with the scapula 110 at the glenoid cavity 120. The acromion 125 and coracoid process 130 extend outwardly from the scapula 110 partially surrounding the head of the humerus 115 and providing mounting surfaces for a number of muscles and tendons (see FIG. 5). The clavicle 135 extends above the scapula 110 and terminates in proximity to the acromion 125.

Figure 3:
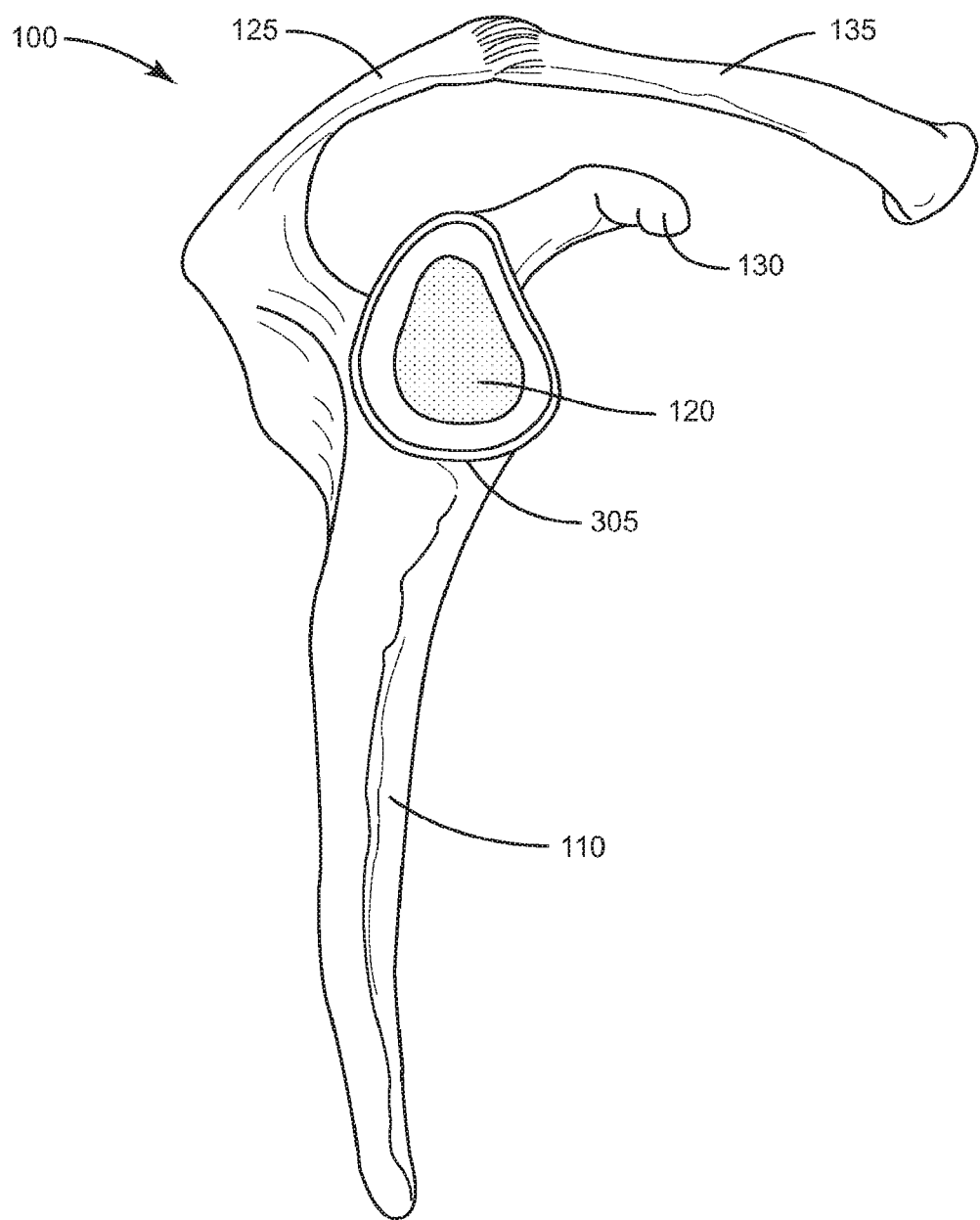
FIG. 3 is a lateral view of the skeletal anatomy of the shoulder.

FIG. 3 illustrates a lateral view of the skeletal anatomy of the shoulder 100 without the humerus 105. In this view, the glenoid cavity 120 is more clearly presented, along with the glenoid labrum 305. The glenoid labrum 305, or glenoid ligament, comprises a fibrocartilaginous rim about the periphery of the glenoid cavity 120. Together, the glenoid cavity 120 and the glenoid labrum 305 form the "socket" of the shoulder ball and socket joint, with the head of the humerus 115 forming the "ball."

Figure 4:
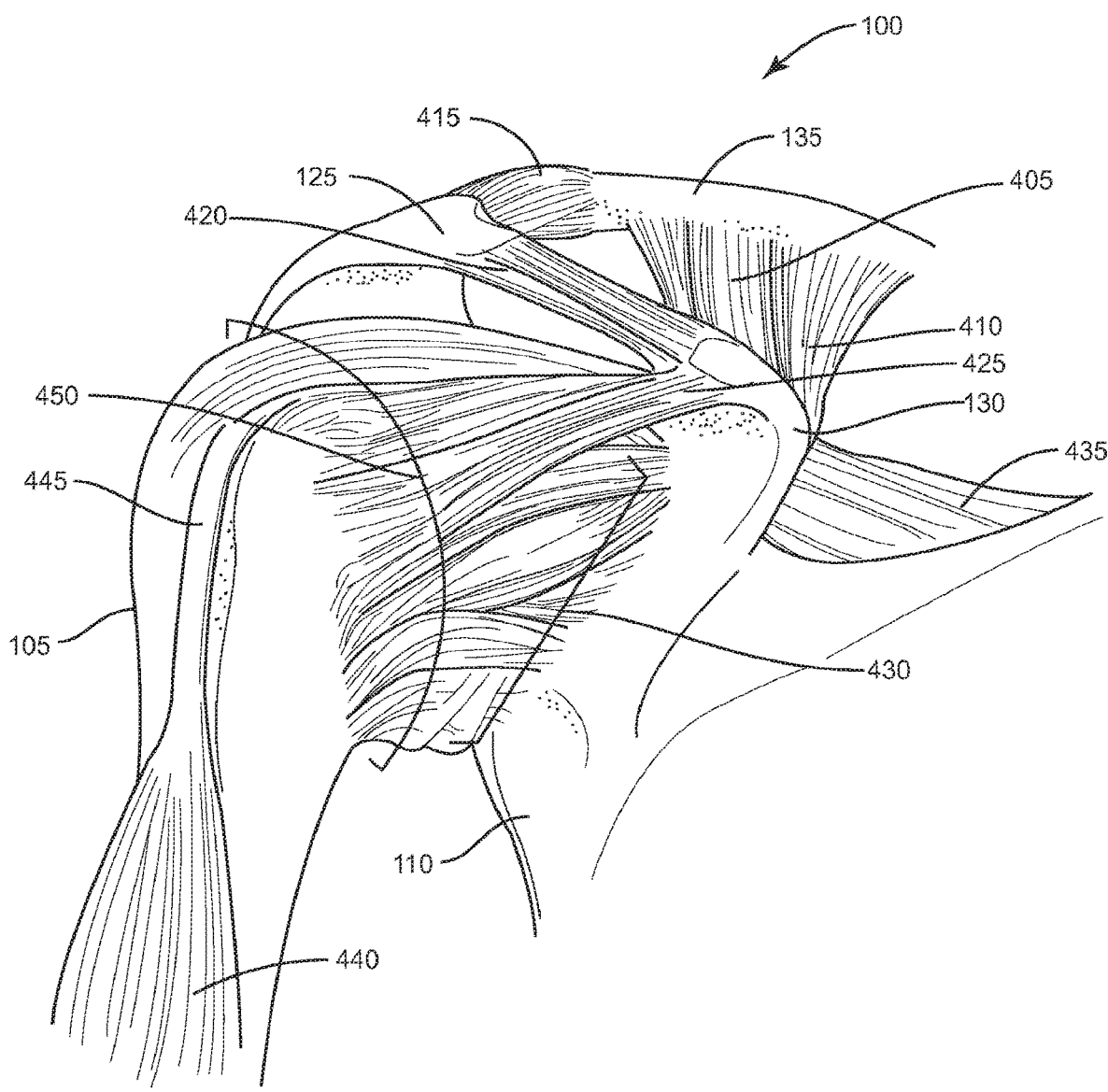
FIG. 4 is an anterior view of the skeletal anatomy of the shoulder and deep level soft tissue.

FIG. 4 illustrates an anterior view of the skeletal anatomy of the shoulder 100 with the deep layer soft tissue (muscles, ligaments, and tendons) present. The coraco-clavicular ligament 405 and the conoid ligament 410 connect the clavicle 135 to the scapula 110 by attaching to the coracoid process 130. The terminal end of the clavicle 135 is connected to the acromion 125 by the acromioclavicular ligament 415. The coracoacromial ligament 420 also connects the coracoid process 130 to the acromion 125. The head of the humerus 115 is connected to the scapula 110 by the coracohumeral ligament 425 that attaches to the coracoid process 130 and the glenohumeral ligaments 430. The supraspinatus muscle 435 runs from the top of the humerus 105 to the scapula 110 and passes between the coracoid process 130 and the acromion 125. The biceps muscle 440 is connected to the shoulder joint 100 by the biceps tendon 445 which attaches to the glenoid labrum 305. The soft tissue generally either connecting or positioned between the humerus 105 and the scapula 110 comprise the rotator cuff 450.

Figure 5:
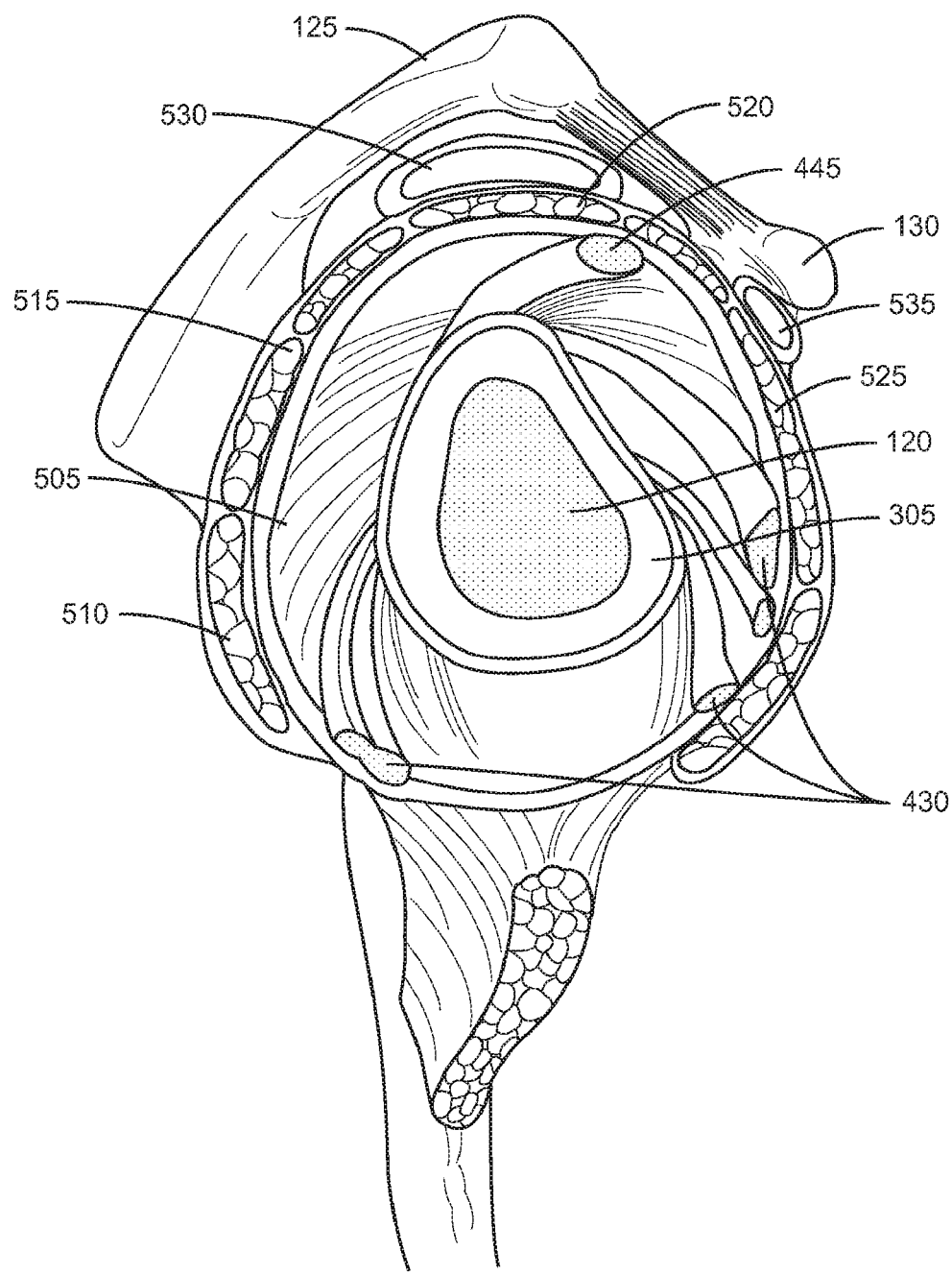
FIG. 5 is a lateral cutaway view of the right shoulder joint socket.

FIG. 5 presents a cut away lateral view of the right shoulder joint 100 to further illustrate the soft tissue. A joint capsule 505 surrounds the ball and socket joint between the head of the humerus 115 and the glenoid cavity 120. The joint capsule 505 provides a watertight sac around the ball and socket joint and provides the main source of stability for the shoulder, holding the ball and socket joint in place and preventing the ball and socket joint from dislocating. Surrounding the joint capsule 505 are a series of muscles including the teres minor muscle 510, the infraspinatus muscle 515, the supraspinatus muscle 520, and the subcapularis muscle 525 that in part form the rotator cuff 450. Positioned between these rotator cuff muscles and the acromion 125 is the subacromial bursa 530. A second bursa, the subcoracoid bursa 535, is positioned between the rotator cuff muscles and the coracoid process 130. The bursae 530, 535 are sacs of lubricating fluid that are positioned where two body parts may rub against one another where there is no joint structure.

Figure 6:
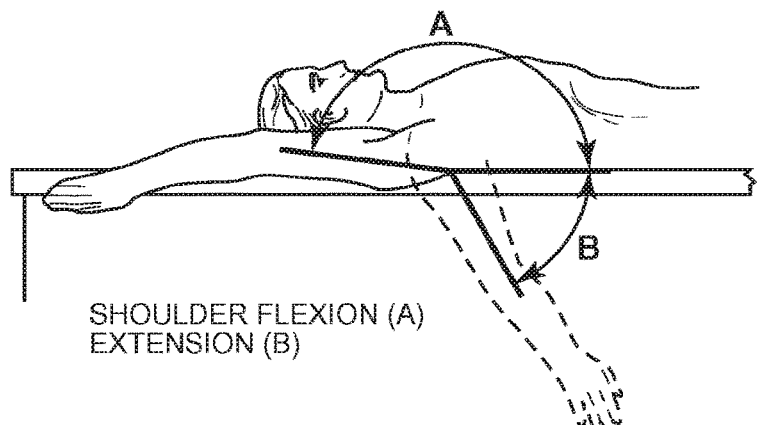
FIG. 6 illustrates arm movement associated with shoulder flexion and extension.
Figure 7:
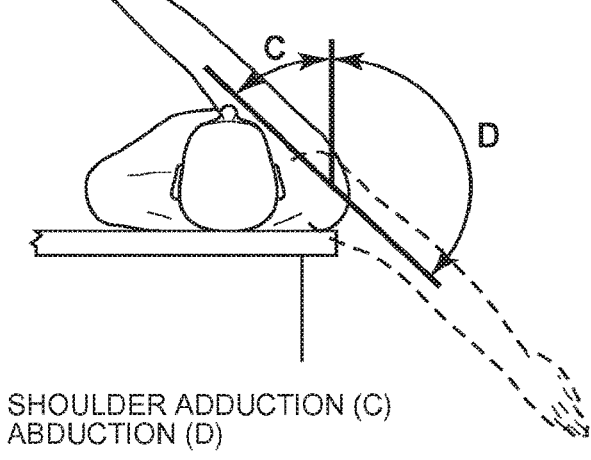
FIG. 7 illustrates arm movement associated with shoulder adduction and abduction.
Figure 8:
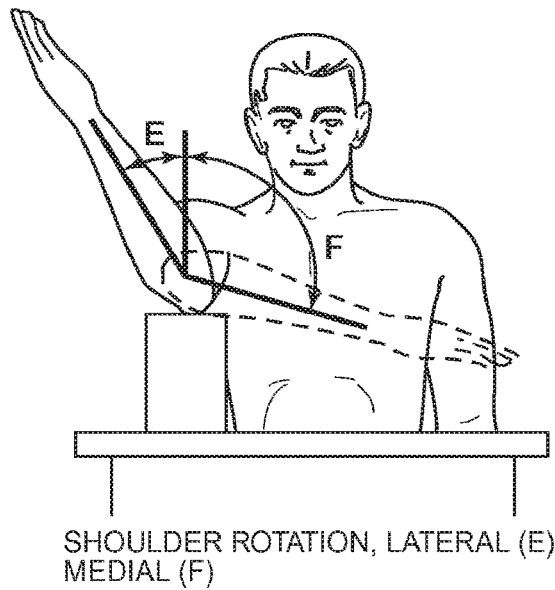
FIG. 8 illustrates arm movement associated with shoulder lateral and medial rotation.

As illustrated above, the glenoid cavity 120 and the glenoid labrum 305 form a relatively shallow socket for receiving the head of the humerus 115. This shallow socket combined with the complex soft tissue structure of the shoulder joint 100 allow a wide range of arm motion which allows the hand to achieve a variety of positions. This range of arm movement involving movement at the shoulder joint 100 is illustrated in FIGS. 6 through 8. FIG. 6 illustrates shoulder flexion (A), or rotation of a straight arm positioned at the side to above the head, and extension (B), or rotation of a straight arm towards the back, without crossing the arm over the torso. The typical range of flexion rotation is about 180 degrees measured from the arm at the side, and typical range of extension rotation is about 50 degrees. FIG. 7 illustrates shoulder adduction (C), or rotation of a straight arm in a raised position and extending straight out from the body across the chest, and abduction (D), or rotation of the same raised straight arm towards the back. The typical range of adduction rotation is about 45 degrees measured from the arm positioned straight out from the body, and the typical range of abduction rotation is about 130 degrees. FIG. 8 illustrates shoulder lateral rotation (E), or rotation of the arm away from the body with the elbow bent at 90 degrees, and medial rotation (F), or rotation of the same bent arm in front of the body. The typical range of lateral rotation is about 60 degrees measured from the forearm positioned upward, and the typical range of medial rotation is about 105 degrees.

As illustrated in FIGS. 6 through 8, the shoulder joint 100 has the widest range of motion of any joint in the body. However, due to the relatively small and shallow size of the socket formed by the glenoid cavity 120 and the glenoid labrum 305, the shoulder joint 100 is inherently unstable and prone to injury as well as a variety of diseases. One common injury is known as impingement syndrome. When the arm is abducted more than about 90 degrees, a projection on the back of the head of the humerus 115 compresses the rotator cuff 450, and in particular the subacromial bursa 530, against the acromion 125 causing pain and loss of range of motion. Additionally, tendonitis associated with the supraspinatus muscles 435 and subacromial bursitis in the subacromial bursa 530 may cause inflammation that compresses the subacromial bursa 530 against the acromion 125.

Another common shoulder injury is a rotator cuff 450 tear. The tear may be in any of the four muscles comprising the rotator cuff 450, or in the surrounding ligaments and tendons. Since the rotator cuff 450 supports essentially all movement of the shoulder, any shoulder movement tends to cause pain when a tear is present.

More severe trauma can lead to broken bones and separated ligaments. For example, a shoulder joint 100 subjected to extreme forces could result in an anterior or posterior dislocation of the head of the humerus 115 from the glenoid cavity 120, a tearing of the glenoid labrum 305, or even a fracture of the head of the humerus 115. Similarly, a partial or complete tear of the acromioclavicular ligament 415, coraco clavicular ligament 405, or conoid ligament 410 associated with the clavicle 135 may result.

The injuries and diseases of the shoulder joint 100 described above, along with a variety of others, can lead to extreme pain when moving the arm and may require surgery and physical therapy. During pre-operative and post-operative periods, as well as during physical therapy, the shoulder joint 100 may cause pain when the arm is moved beyond a limited range of motion before healing is completed. Painful movements may be exacerbated when the injured person is lying down and trying to sleep because the arm may be moved considerably in order to find a comfortable position. While an arm sling may be worn while sleeping, the position of the arm in the sling (generally medially rotated, see FIG. 8) while lying down tends to drive the head of the humerus 115 upwards into the rotator cuff 450 which tends to cause pain and discomfort.

Figure 9:
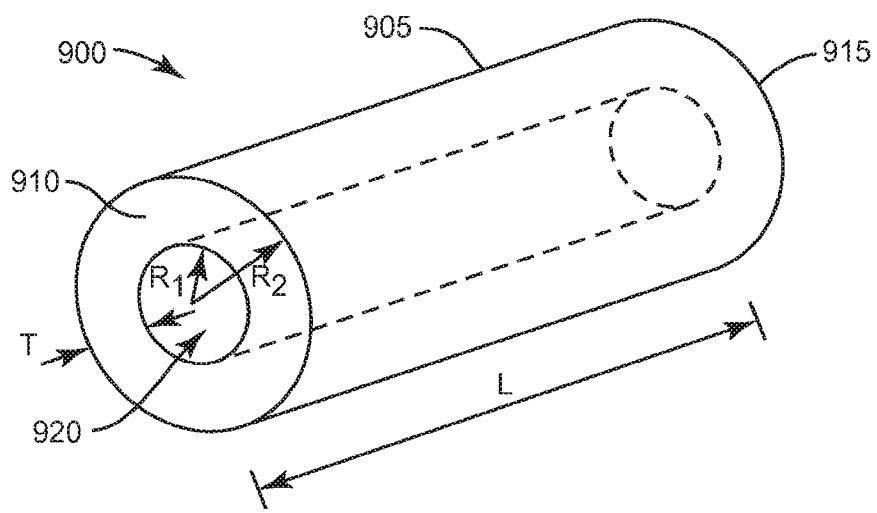
FIG. 9 is a perspective view of an arm movement restraining device according to various embodiments.

FIG. 9 illustrates various embodiments of an arm movement restraining device 900 that may be worn while lying down to restrict movement of the arm such that impingement or other excessive movements of the shoulder joint 100 may be reduced. The restraining device 900 may comprise a generally tubular body or cuff 905. The body 905 may comprise an inner radius R1 defining an open axial passage 920 extending through the body 905 from a proximal end 910 to a distal end 915. The inner radius R1 may be selected such that the restraining device 900 may fit comfortably on a forearm of the user. Generally, the fit of the restraining device 900 is such that the restraining device 900 is tight enough to stay on forearm without slipping off but loose enough so that blood flow in the forearm is not impeded. The value of R1 may vary from about 2 inches to about 6 inches depending on the size of the forearm.

In various embodiments, the body 905 may also comprise an outer radius R2 that, in conjunction with the inner radius R1, defines a wall thickness T of the body 905. As discussed in further detail below, the outer radius R2 may be selected to provide a wall thickness T sufficient to restrict movement of the arm while the user is lying down such that rotational movement of the shoulder is minimized, thereby reducing shoulder impingement. The wall thickness T may be selected based on a variety of factors including, but not limited to, height, weight, gender, and physical condition of the user; desired amount of arm movement desired; length of forearm; length of upper arm; typical sleeping position of the user (on the back, side, or stomach); and the like. Generally, the wall thickness T may range from about 2 inches to about 10 inches, and the corresponding outer radius R2 may range from about 5 inches to about 16 inches. In various embodiments, the wall thickness T may be selected to limit shoulder flexion, extension, adduction, abduction, lateral rotation, and medial rotation are each limited to a maximum of about 30 degrees when the restraining device 900 is engaged on the forearm of the user.

The body 905 may have a length L selected such that the proximal end 910 is positioned in proximity to the user's elbow, and the distal end 915 is positioned in proximity to the user's wrist when the restraining device 900 is placed on the user's forearm. In general, the length L is greater than a length of the user's upper arm. For adult users the length may range from about 5 inches to about 16 inches. For child or adolescent users, a reduced length L may be required. As will be evident to one skilled in the art, any inner radius R1, outer radius R2, wall thickness T, length L, and combinations thereof, are within the scope of this disclosure.

Figure 10:
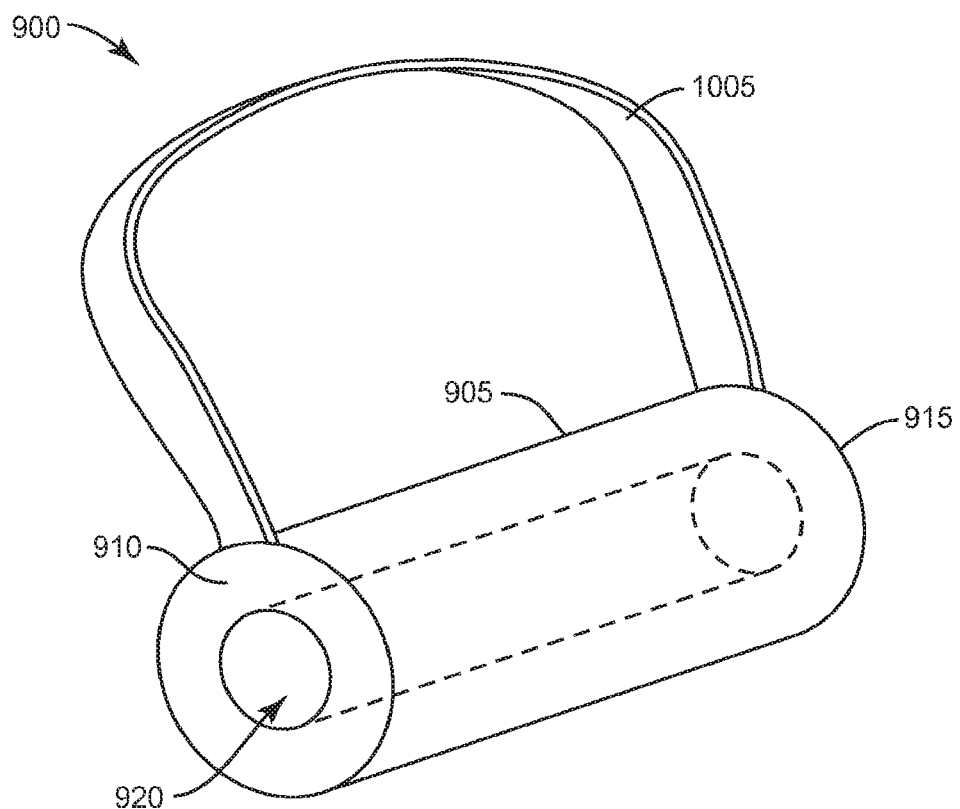
FIG. 10 is a perspective view of an arm movement restraining device according to various embodiments.

FIG. 10 illustrates various embodiments of the restraining device 900 comprising a strap 1005. The strap 1005 may be placed over the shoulder of the user to function as a sling, for example, to support the arm and the weight of the restraining device 900 should the user get out of bed for a short period of time. The strap 1005 may also be adapted for placement about the waist of the user to further restrain movement of the arm.

Figure 11:
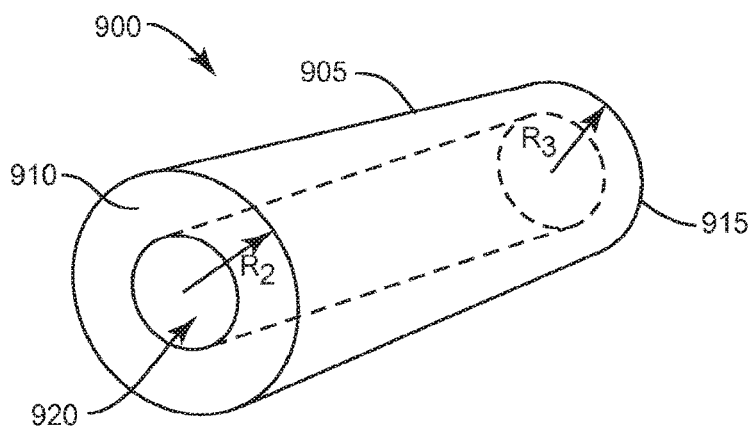
FIG. 11 is a perspective view of an arm movement restraining device according to various embodiments.
Figure 12:
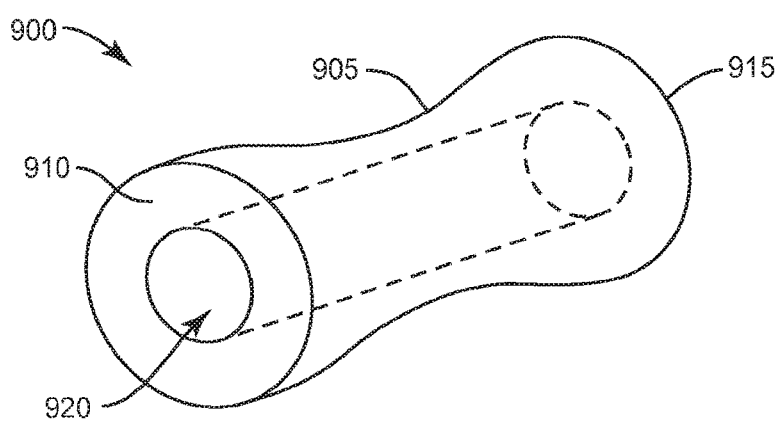
FIG. 12 is a perspective view of an arm movement restraining device according to various embodiments.

Although FIGS. 9 and 10 illustrate the body 905 being generally cylindrical with parallel side walls, other shapes are contemplated and within the scope of the present disclosure. For example, FIG. 11 illustrates various embodiments in which the wall thickness T decreases from the proximal end 910 to the distal end 915 such that the outer radius R2 at the proximal end is greater than an outer radius R3 at the distal end. The tapered design of FIG. 11 may be more comfortable for some users by not elevating the hand as much as the design illustrated in FIG. 9. Similarly, FIG. 12 illustrates various embodiments in which the body 905 has an hourglass shape, which may be more comfortable if the user places their arm across their stomach while lying down.

Figure 13:
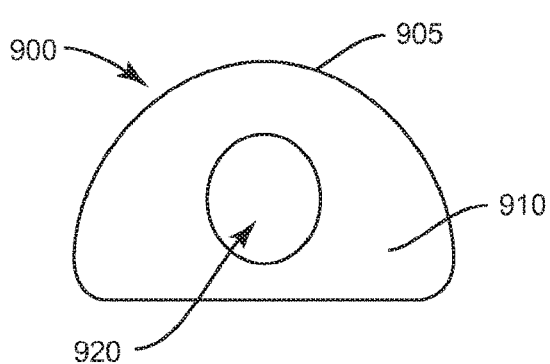
FIG. 13 is an end view of an arm movement restraining device according to various embodiments.
Figure 14:
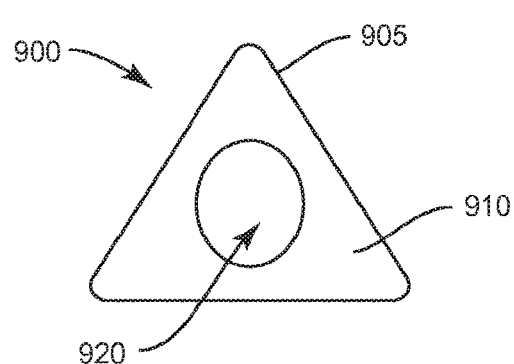
FIG. 14 is an end view of an arm movement restraining device according to various embodiments.

FIGS. 13 and 14 illustrate various embodiments in which a cross-section of the body 905 is not generally circular. In FIG. 13, a portion of the outer surface of the body 905 may be flattened which may provide more stability while the user is lying down. FIG. 14 illustrates that the cross-sectional shape of the body 905 need not be rounded or circular at all, and may comprise a plurality of generally flat surfaces.

Figure 15:
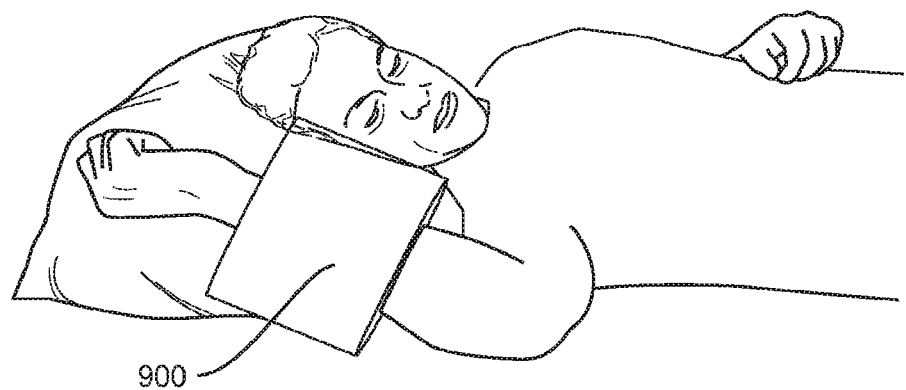
FIG. 15 illustrates a person in a lying position with an arm movement restraining device engaged on a forearm.
Figure 16:
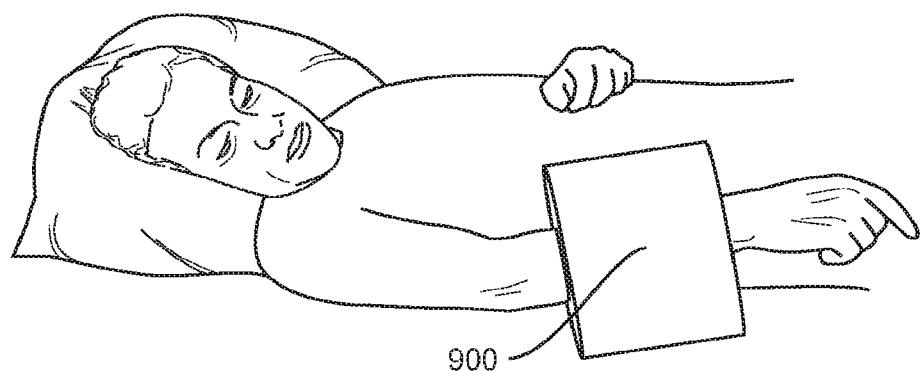
FIG. 16 illustrates a person in a lying position with an arm movement restraining device engaged on a forearm.

FIGS. 15 through 20 illustrate the user in a variety of lying positions with the restraining device 900 engaged on the forearm corresponding to an injured or diseased shoulder according to various embodiments. FIG. 15 illustrates the user lying on his back with the right shoulder as the affected shoulder. In this position, the right arm may tend to laterally and medially rotate to the extremes, which may cause immediate pain and prevent or disturb sleep. The restraining device 900 may tend to restrict rotation within a more manageable range. In addition, maintaining the arm in a neutral position (with reference to lateral and medial rotation) to minimize impingement is an unnatural position. The restraining device 900 may buttress the arm in place without immobilizing the shoulder joint 100 making it easier for the user to maintain the neutral position. Further, in FIG. 16 the user may try to fully extend the right arm along his side. The restraining device 900 may contact the bed and prevent the arm from fully extending because maintaining a slightly bent elbow while lying on the back may reduce pressure on the shoulder joint 100.

Figure 17:
FIG. 17 illustrates a person in a lying position with an arm movement restraining device engaged on a forearm.

FIG. 17 illustrates the user lying on the right side with the left shoulder being the affected shoulder. In this case, the restraining device 900 may prevent the user from rolling over on his stomach with his left arm underneath. Rolling over on his stomach may force the arm to fully rotate medially, putting sudden and intense pressure on the shoulder joint 100 which may result in significant pain and perhaps further injury.

Figure 18:
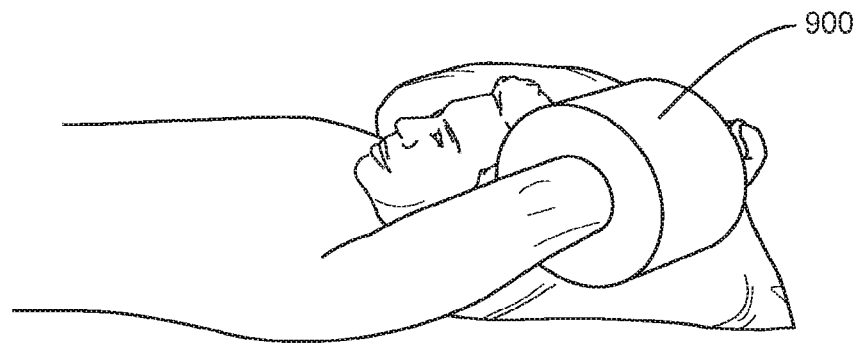
FIG. 18 illustrates a person in a lying position with an arm movement restraining device engaged on a forearm.
Figure 19:
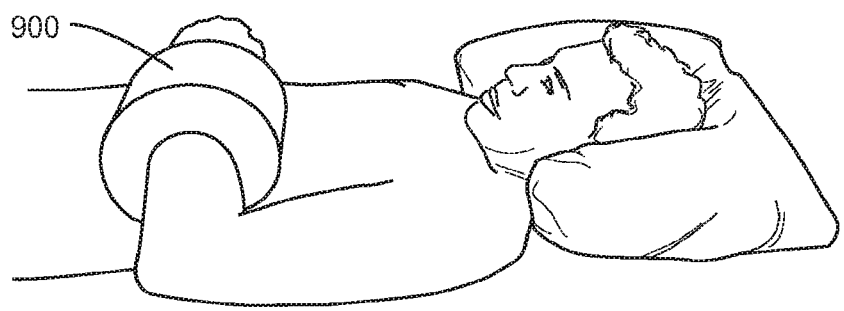
FIG. 19 illustrates a person in a lying position with an arm movement restraining device engaged on a forearm.

In FIGS. 18 and 19, the user is lying on his back and moves the arm from a flexion position (FIG. 18) to an extension position (FIG. 19) while maintaining a bend in the elbow. The restraining device 900 stops the shoulder joint 100 from full flexion rotation in FIG. 18, and provides a natural and comfortable neutral position when the arm is extended as in FIG. 19.

Figure 20:
FIG. 20 illustrates a person in a lying position with an arm movement restraining device engaged on a forearm.

In FIG. 20, the user is lying on the right side, which is the side with the affected shoulder. To relieve impingement, the user should place the right arm in a neutral position at his side; however, that is an unnatural position. The user may tend to extend the right arm such that the right hand is above the head, but this position will cause impingement and resulting pain, making sleep difficult. However, with the restraining device 900 on the right forearm, flexion rotation of the arm is restricted and impingement does not occur or may be significantly reduced.

Figure 21A:
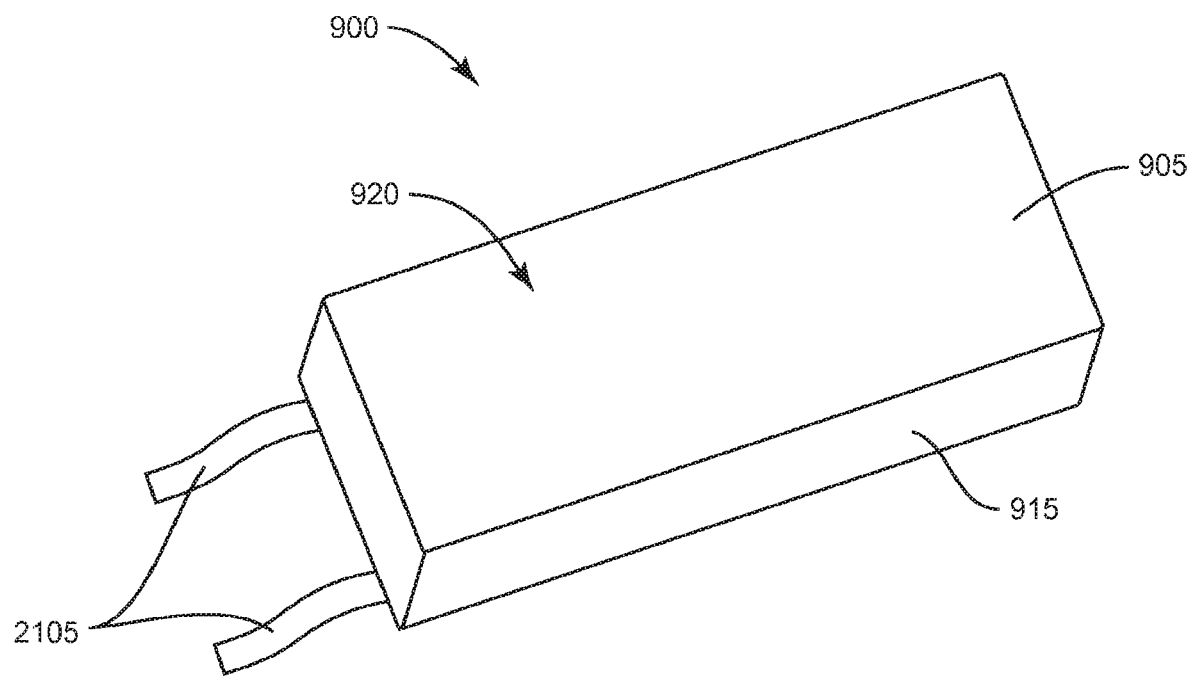
FIG. 21A is a perspective view of an arm movement restraining device according to various embodiments.
Figure 21B:
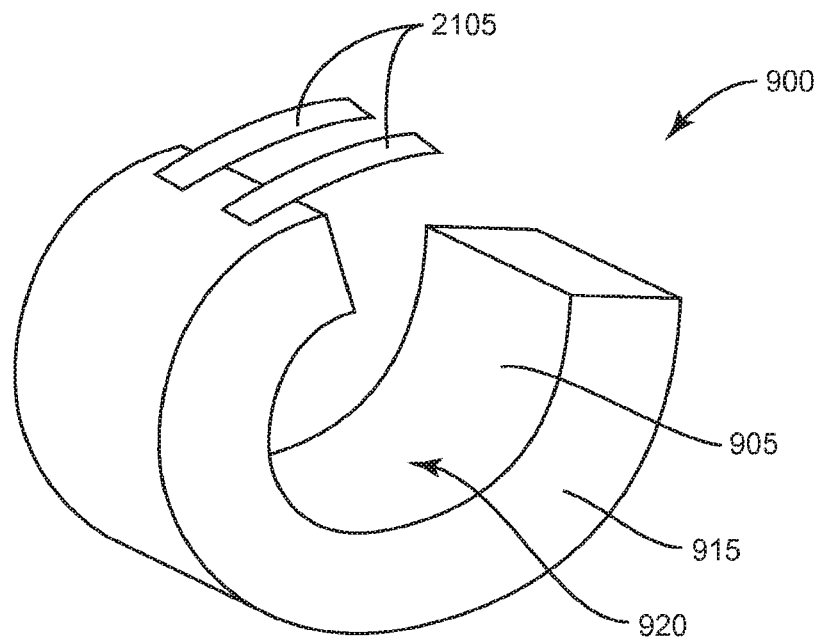
FIG. 21B is a perspective view of an arm movement restraining device according to various embodiments.

In various embodiments as illustrated in FIGS. 21A and 21B, the body 905 of the restraining device 900 may be obtained by the user in a flat sheet form that the user rolls (FIG. 21B) into a cylindrical shape and secures the body 905 with closure straps 2105 (or other closure mechanism). Thus, the user may adjust the tightness of the restraining device 900 on the forearm by loosening or tightening the closure straps 2105.

Although not shown in the drawings, the body 905 may contain an internal void. The void may comprise a bladder that may be filled with gas or liquid to inflate the body 905 to the desired wall thickness T, as well as adjust the pressure exerted on the forearm. In other embodiments, the void may be filled with a cold or hot pack, or a pack adapted to dispense pharmaceutical agents.

The body 905 may be constructed of a lightweight foam such as polyethylene, urethane, polyurethane, neoprene, polystyrene, latex, or any combination thereof. The material of construction may be chosen such that the foam will not collapse an appreciable amount under the weight of the user's arm, thereby generally maintaining the outer radius R2.

Figure 22:
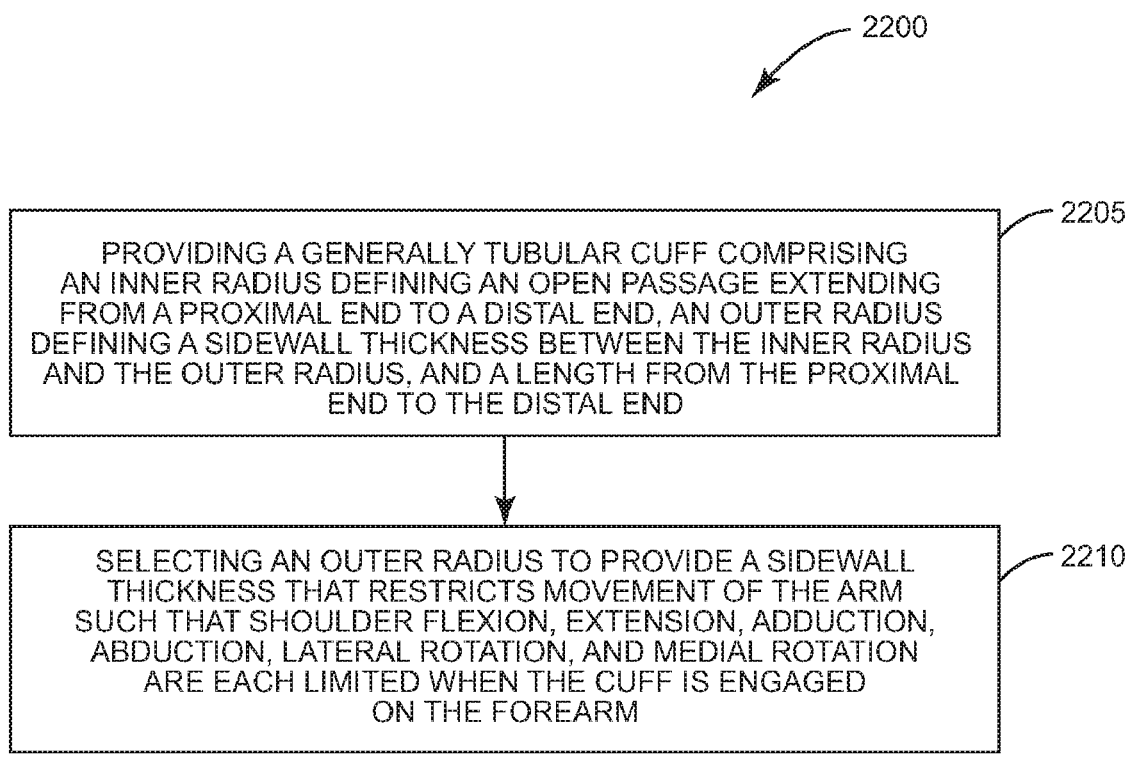
FIG. 22 is an exemplary flow diagram of a method for reducing shoulder impingement for a person in a lying position according to various embodiments.

FIG. 22 illustrates a general flow chart of various embodiments of a method 2200 for reducing shoulder impingement for a person in a lying position. At step 2205, a generally tubular body or cuff 905 may be provided. The body 905 may comprise an inner radius R1 defining an open axial passage 920 extending axially from a proximal end 910 to a distal end 915. The opening axial passage 920 may be adapted to releasably engage a forearm of the person therein. The body 905 may further comprise an outer radius R2 defining a sidewall thickness between the inner radius R1 and the outer radius R2, and may comprise a length L from the proximal end to the distal end.

At step 2210, the outer radius R2 may be selected to provide a sidewall thickness T that restricts movement of the person's arm such that shoulder flexion, extension, adduction, abduction, lateral rotation, and medial rotation are each limited when the body 905 is engaged on the forearm. In various embodiments, the shoulder flexion, extension, adduction, abduction, lateral rotation, and medial rotation are each limited to a maximum of 30 degrees.

Figure 23:
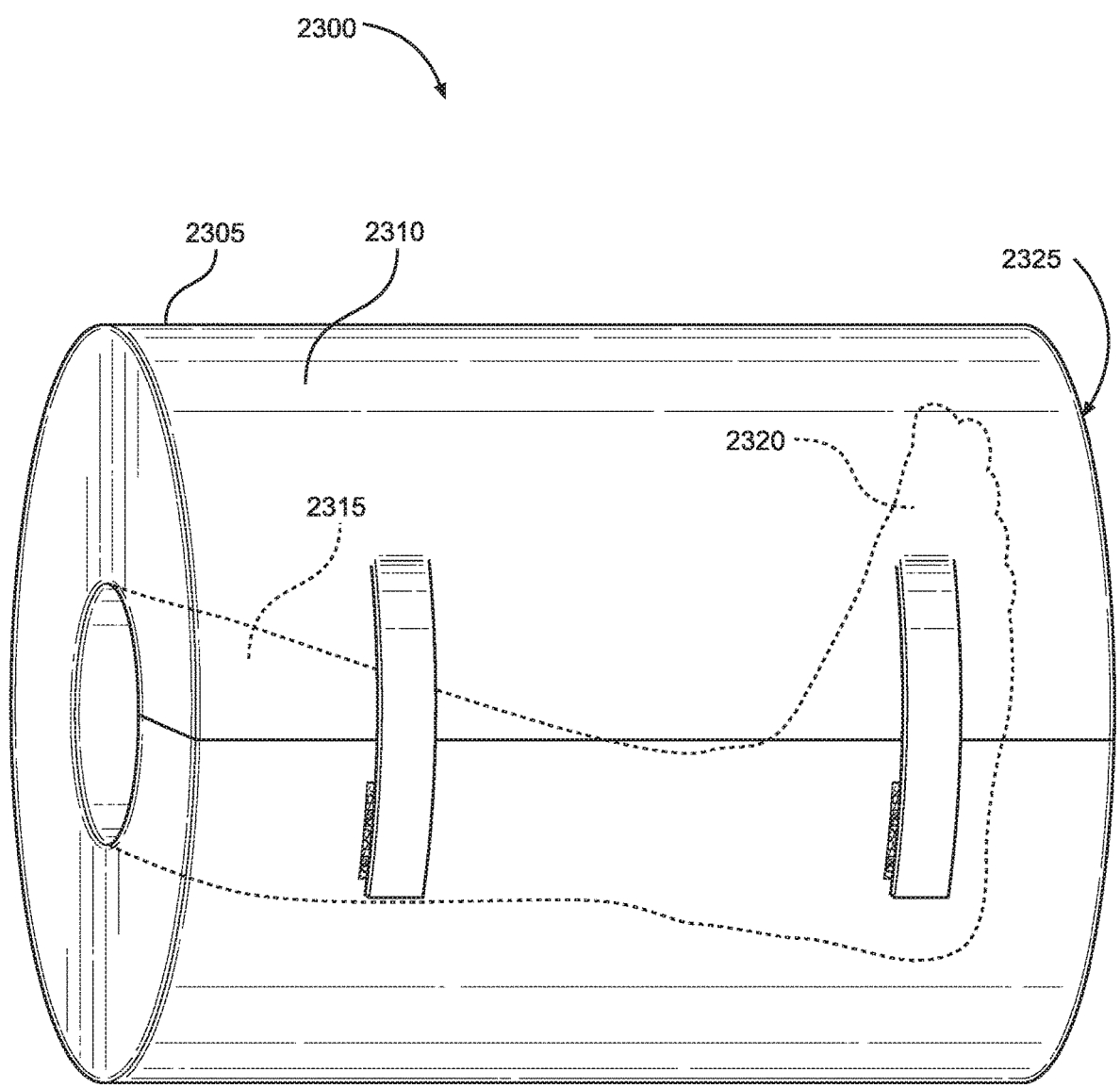
FIG. 23 is a perspective view of a foot movement restraining device according to various embodiments.

FIG. 23 is a perspective view of a foot movement restraining device according to various embodiments.

Shown in FIG. 23 is a generally cylindrical cuff 2300, outer diameter 2305, optional vent 2310, inner radius 2315, foot position 2320, and bottom end enclosure 2325. An opening with Velcro® straps in order to get the leg in and out of the brace is also shown.

Dorsiflexion is the movement of the foot upwards, so that the foot is closer to the shin. For a movement to be considered dorsiflexion, the foot should be raised upward between 10 and 30 degrees. Dorsiflexion uses the muscles in the front part (anterior) of the foot. The tendons of the muscles that pass through the front of the foot and into the ankle joint include the tibialis anterior, extensor hallucis longus, and extensor digitorum longus. These tendons are located on the front of the leg and are supplied by the deep peroneal nerve. Damage to this nerve can stop a person from being able to raise their foot.

Plantar fasciitis is one of the most common causes of heel pain. It involves inflammation of a thick band of tissue that runs across the bottom of the foot and connects the heel bone to the toes (plantar fascia).

People use dorsiflexion when they walk. During the middle stages of weight bearing and just before pushing off the ground, the foot will reach its end range of dorsiflexion. If there are problems with dorsiflexion, then the body will compensate naturally, which in turn can cause issues elsewhere.

Referring again to FIG. 23, according to various exemplary embodiments, a method for maintaining a foot in a neutral dorsiflexion position 2320 for a person in a lying position comprises providing a generally cylindrical cuff 2300 extending from a proximal end of a person's leg just below the person's knee cap to an inner distal end near the person's foot bottom, the generally cylindrical cuff 2300 comprising an inner radius 2315 defining an open passage through the generally cylindrical cuff 2300. The passage is configured to releasably engage the foot of the person in the neutral dorsiflexion position 2320. A generally round bottom enclosure 2325 is selected at an outer distal end near the person's foot bottom and perpendicular to the generally cylindrical cuff for enclosing the foot. An outer diameter 2305 of the generally cylindrical cuff is selected to provide a sidewall thickness that restricts movement of the foot of the person, and elevates the person's leg without elevating the person's knee to limit knee flexion when the generally cylindrical cuff is releasably engaged on the foot of the person.

Figure 24:
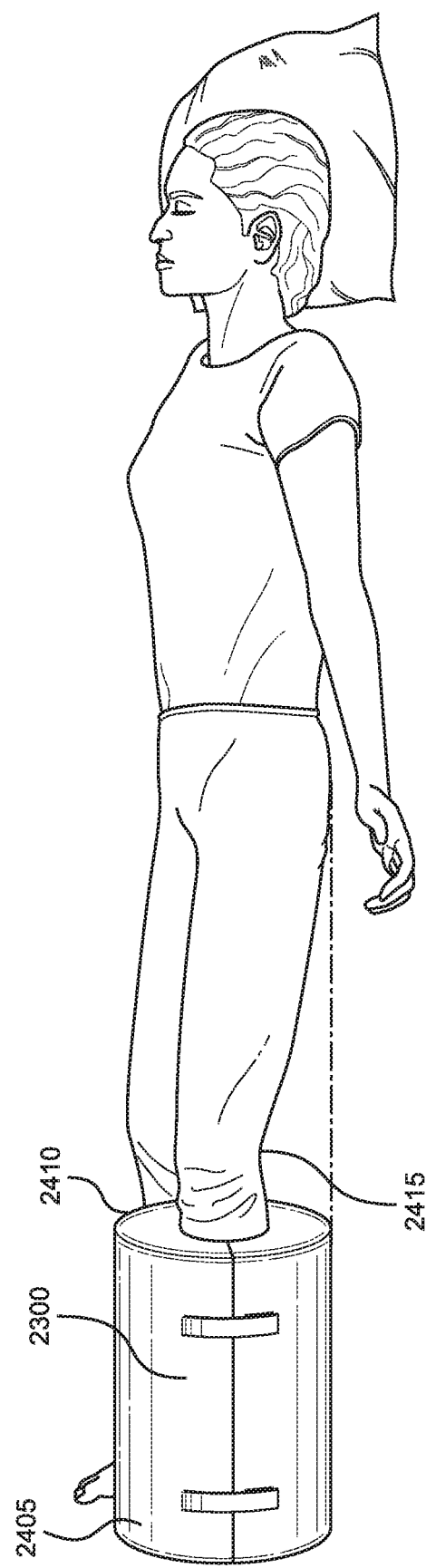
FIG. 24 is another perspective view of a foot movement restraining device according to various embodiments.

FIG. 24 is another perspective view of a foot movement restraining device according to various embodiments.

Shown in FIG. 24 is the generally cylindrical cuff 2300, distal end 2405, proximal end 2410 and knee flex 2415. An opening with Velcro® straps in order to get the leg in and out of the brace is also shown.

In various exemplary embodiments, the proximal end 2410 is near the knee cap of the person and the distal end 2405 is near the toes of the person when the device is positioned on the foot of the person. The sidewall thickness may range from about 3 inches to about 8 inches. Furthermore, the generally cylindrical cuff 2300 may be constructed of a lightweight foam material, including polyethylene, urethane, polyurethane, neoprene, polystyrene, latex, or a combination thereof. According to further exemplary embodiments, the cuff may comprise an inflatable bladder to vary the inner radius, thereby adjusting an amount of pressure exerted on the foot. The generally cylindrical cuff 2300 may further comprise an inflatable bladder to vary the outer radius. The generally cylindrical cuff 2300 may exude one or more pharmaceutical agents, or apply heat or cold.

As shown in FIG. 24, according to exemplary embodiments, the foot is maintained in a neutral dorsiflexion position 2320 (FIG. 23) for a person in a lying position. Accordingly, it allows the person to turn in bed from side to side or from front to back. The device also maintains elevation. In further exemplary embodiments, the cuff may be vented for comfort.

In most exemplary embodiments, the device does not limit knee flexion. Additionally, the device may be used to cover a cast for cleanliness or comfort, or may be used as a plantar fasciitis splint.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "proximal", "distal", and the like, are also used to describe various elements, regions, sections, etc. and are also not intended to be limiting. Like terms refer to like elements throughout the description.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method for maintaining a foot in a neutral dorsiflexion position for a person in a lying position, comprising steps of:
   providing a generally cylindrical cuff configured to extend from a proximal end of a person's leg adjacent to the person's knee cap to an inner distal end near the person's foot bottom, the generally cylindrical cuff comprising an inner radius defining an open passage through the generally cylindrical cuff, the open passage configured to releasably engage the foot of the person in the neutral dorsiflexion position;
   selecting a generally round bottom enclosure at an outer distal end near the person's foot bottom and perpendicular to the generally cylindrical cuff for enclosing the foot; and
   selecting an outer diameter of the generally cylindrical cuff to provide a sidewall thickness that restricts movement of the foot of the person, elevates the person's leg without elevating the person's knee to limit knee flexion when the generally cylindrical cuff is releasably engaged on the foot of the person.

2. The method of claim 1, the maintaining of the neutral dorsiflexion position of the foot generally comprising the person's foot being straight up and at a right angle to the leg.

3. The method of claim 1, further comprising the selecting of the outer diameter of the generally cylindrical cuff to provide a sidewall thickness that allows the generally cylindrical cuff to rotate with a body of the person when it is releasably engaged on the person's foot and the person is in the lying position.

4. The method of claim 1, further comprising the selecting of the outer diameter of the generally cylindrical cuff to provide a sidewall thickness that allows the person's other foot that is not in a cuff to rest on top of the generally cylindrical cuff when the person is in the lying position.

5. The method of claim 1, further comprising the generally cylindrical cuff enhancing recovery of an injured leg or ankle.

6. The method of claim 1, further comprising selecting a generally cylindrical cuff that is solid or vented.

7. The method of claim 6, further comprising the vented generally cylindrical cuff having openings for air circulation.

8. The method of claim 1, wherein the elevating of the person's leg without elevating the person's knee to limit knee flexion further comprising positioning the generally cylindrical cuff four to six inches below the person's knee.

9. The method of claim 1, further comprising selecting an inner radius to accommodate a cast.

10. The method of claim 9, further comprising increasing a cushioning of the cast.

11. The method of claim 10, further comprising increasing the cleanliness of the cast.

12. The method of claim 1, further comprising using the generally cylindrical cuff as a night splint.

13. The method of claim 1, further comprising using the generally cylindrical cuff to treat plantar fasciitis.

14. The method of claim 1, wherein the generally cylindrical cuff is constructed of a lightweight foam material.

15. The method of claim 14, wherein the foam material comprises polyethylene, urethane, polyurethane, neoprene, polystyrene, latex, or a combination thereof.

16. The method of claim 1, wherein the generally cylindrical cuff further comprises an inflatable bladder to vary the inner radius thereby adjusting an amount of pressure exerted on the foot.

17. The method of claim 1, wherein the generally cylindrical cuff further comprises an inflatable bladder to vary an outer radius.

18. The method of claim 1, wherein the generally cylindrical cuff exudes one or more pharmaceutical agents.

19. The method of claim 1, wherein the generally cylindrical cuff is adapted to apply heat or cold.

* * * * *